United States Patent [19]

Schanen

[11] Patent Number: 5,218,533
[45] Date of Patent: Jun. 8, 1993

[54] STABLE INTERRUPTIBLE FILTER FOR DUAL BEAM COMPUTED TOMOGRAPHY

[75] Inventor: Paul C. Schanen, Waukesha, Wis.

[73] Assignee: General Electric Company, Milwaukee, Wis.

[21] Appl. No.: 562,766

[22] Filed: Aug. 6, 1990

[51] Int. Cl.$^5$ ............................................. G06F 15/00
[52] U.S. Cl. ................................................ 364/413.15
[58] Field of Search ..................... 364/413.15, 413.14, 364/413.15, 413.16, 413.17

[56] References Cited

U.S. PATENT DOCUMENTS

| | | | |
|---|---|---|---|
| 4,029,963 | 6/1977 | Alvarez et al. | 250/360 |
| 4,331,877 | 5/1982 | Barrett et al. | 250/445 T |
| 4,393,352 | 7/1983 | Volpe et al. | 329/50 |
| 4,547,893 | 10/1985 | Gordon | 378/19 |
| 4,583,240 | 4/1986 | Gatten et al. | 378/19 |
| 4,620,313 | 10/1986 | Erker | 378/19 |
| 4,815,118 | 3/1989 | Acharya et al. | 378/19 |
| 5,115,394 | 5/1992 | Walters | 364/413.17 |

FOREIGN PATENT DOCUMENTS 0134962 3/1985 European Pat. Off.
2299650 8/1976 France.

Primary Examiner—Roy N. Envall, Jr.
Assistant Examiner—Ari M. Bai
Attorney, Agent, or Firm—Quarles & Brady

[57] ABSTRACT

A data acquisition filter for a dual beam CT machine uses two spectral filters for alternately receiving the signal from each detector depending on the state of the x-ray beam. When one filter is filtering the detector signal, the other filter is in a "hold" state where its output and internal values are frozen. Each filter effectively filters only the signal occurring during one beam state without being effected by the signal occurring during the other beam state or by the passage of time during the other beam state The output of the filter in the holding state is constant and may be sampled at any time during this period.

9 Claims, 4 Drawing Sheets

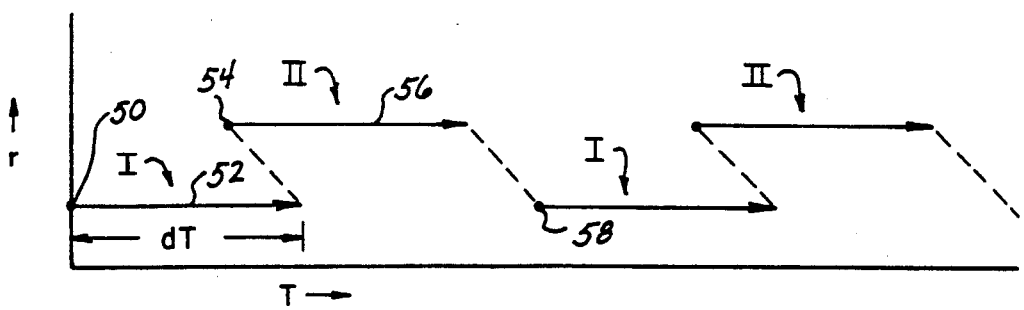
FIG. 3
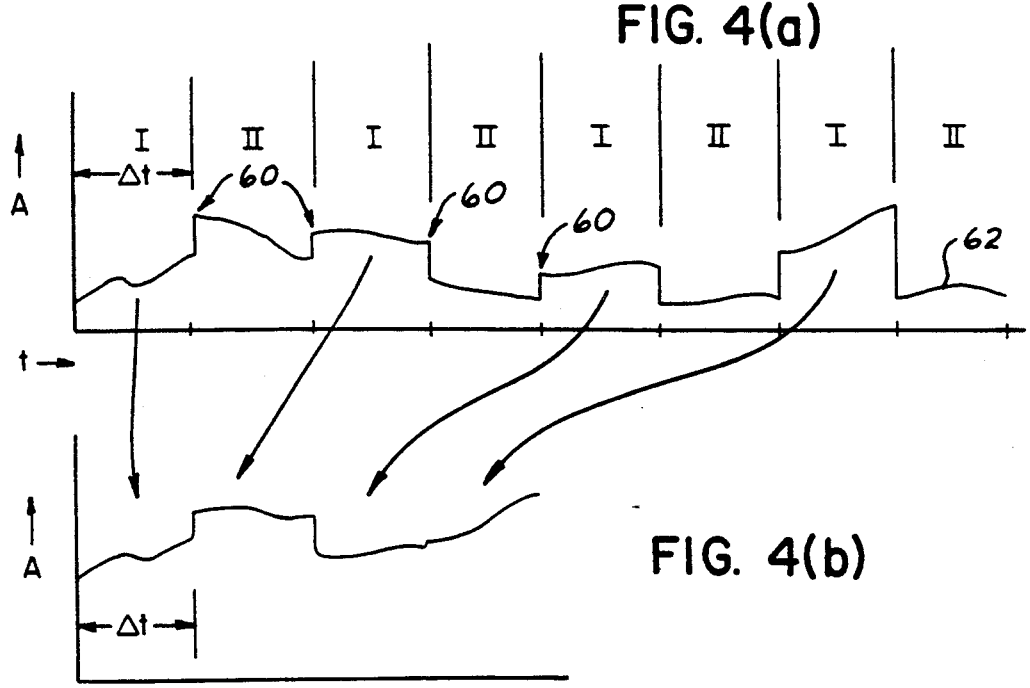
FIG. 4(a)
FIG. 4(b)
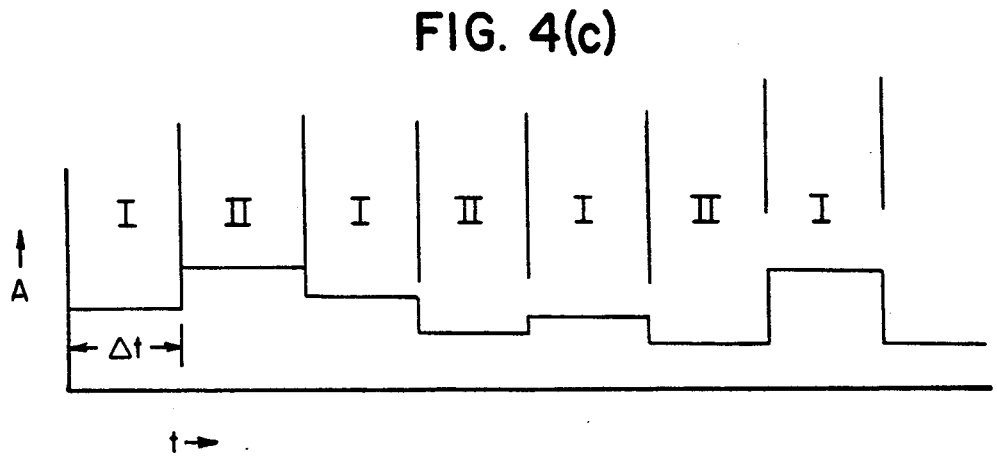
FIG. 4(c)

STABLE INTERRUPTIBLE FILTER FOR DUAL BEAM COMPUTED TOMOGRAPHY

BACKGROUND OF THE INVENTION

This invention relates to computed tomography (CT) systems and specifically to an anti-aliasing filter for use in processing the data collected by a CT system.

In a computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array oriented within the imaging plane.

The detector array is comprised of detector elements separated by a pitch approximately equal to their width. Each detector element measures the intensity of transmitted radiation along a beam projected from the x-ray source to that particular detector element. The intensity of the transmitted radiation is dependent on the attenuation of the x-ray beam along that ray by the imaged object.

The x-ray source and detector array may be rotated on a gantry within the imaging plane and around the imaged object so that the angle at which the fan beam intersects the imaged object constantly changes. As the gantry rotates, a number of projections forming a projection set are acquired, each projection made up of the intensity signals from the detector elements as they travel over a small angle of gantry rotation centered around a projection angle.

The acquired tomographic projection sets are typically stored in numerical form for computer processing to "reconstruct" a slice image according reconstruction algorithms known in the art. A projection set of fan beam projections may be reconstructed directly into an image by means of fan beam reconstruction techniques, or the intensity data of the projections may be sorted into parallel beams and reconstructed according to parallel beam reconstruction techniques. The reconstructed tomographic images may be displayed on a conventional CRT tube or may be converted to a film record by means of a computer controlled camera.

The continuous rotation of the gantry produces a constantly changing signal from each detector corresponding to the variation of attenuation of the x-ray beam associated with that detectors as the angle of the x-ray beam changes. This signal may be integrated over the increment of gantry rotation associated with each projection angle to produce the detector signal for that projection angle. This integrated value is then held for sampling and conversion to a digitized detector value by a data acquisition system ("DAS") for storage and reconstruction by a computer.

The integration of the detector signal increases the sensitivity of the detectors and also provides an intrinsic bandlimiting of the detector signal to prevent "aliasing" during the sampling of the detector signal by the DAS. As is understood in the art, aliasing is a signal artifact produced by frequency components in a sampled signal having a frequency higher that half the sampling rate.

In order to provide adequate time for the sampling of each detector signal by the DAS, two such integrators may be used with each detector element. One integrator holds the value of previously integrated data for sampling while the other integrator integrates new current data from the detector element. This two integrator design is termed "integrate and dump" and has the advantage of providing a well defined integration time and a generous sampling window for the DAS.

Nevertheless, the integrate and dump circuit is susceptible to variations in gain caused by changes in the value of its integrating capacitor. Further, the solid state switches typically used to alternately connect the two integrators have significant leakage currents and require that the detector signal first be preamplified. Variations in the gain of this independent preamplifier contributes to the gain variations experienced with the integrate and dump design. Variations in gain can cause unacceptable streaking, "o-rings", smudges or other artifacts in the reconstructed tomographic image.

A continuous wave filter, such as a low pass filter, may be used in place of an integrator. In a continuous wave filter the filter output reflects the previous detector signal on a weighted rolling basis. The use of a low pass filter with an appropriate frequency cutoff point eliminates aliasing.

The operation of the continuous wave filter is such that sampling may occur at any time, provided an appropriate correction is made for gantry position, and hence only a single filter is required for each detector. This eliminates the need for an independent preamplifier associated with the solid state switches of the integrate and dump circuit.

The use of a continuous wave filter provides improved gain stability over the integrate and dump design. Direct current feedback may be established around the continuous wave filter (unlike an integrator) and therefore, the gain of the filter may be fixed by a single resistor as opposed the capacitor of the integrate and dump circuit and the resistor of its associated preamplifier. Resistors are generally more stable than capacitors and one element is generally more stable than multiple elements.

With certain CT imaging techniques, the x-ray beam switches rapidly between two beam intensities or two beam positions during the rotation of the gantry. In dual energy scanning, for example, the power to the x-ray tube may be varied to a produce two x-ray beams having different spectra to create two images whose comparison may be useful for distinguishing between various tissue types. Alternatively, in "spot wobble" scanning, the point of x-ray emission may be "wobbled" with respect to the gantry to create two beams with slightly different angles to increase the resolution of the x-ray image. This latter technique is described in detail in U.S. application Ser. No. 07/540,995 filed Jun. 20, 1990, entitled: "Computed Tomography System with Translatable Focal Spot", assigned to the same assignee as the present invention and hereby incorporated by reference.

In each of these dual beam techniques, the beam is rapidly shifted between states as the gantry rotates so as to lessen the effects of movement by the patient on the consistency of the data collected. Such patient movement generally causes more variations between corresponding detector signals when the state of the beam is shifted only between full revolutions of the gantry.

With the rapid shifting of the x-ray beam, the signal from the detectors also changes and must be separated in synchronism with the shifting of the beam so as to collect two distinct sets of data, one associated with each beam state. One way to separate the detector signals associated with each state of the beam is to use the previously described dual integrators of the integrate and dump circuit. The first integrator is adjusted to integrate (and hence to collect data) only during the first state of the beam, and the second integrator is adjusted to integrate only during the second state of the beam. The outputs of the integrators produce two distinct sets of detector data one associated with each beam state.

Unfortunately, this approach still carries the drawbacks of gain sensitivity associated with the integrate and dump circuit as previously described, i.e. the gain of the circuit is determined by a relatively unstable capacitor value associated with each integrator and a resistor associated with a separate preamplifier.

The continuous wave filter, previously described, is not suitable for these dual beam techniques because the filter produces a continuous output that is a function of previous detector signals regardless of the beam state. The continuous nature of the continuous wave filter, which previously worked to its advantage by allowing flexible sampling, prevents clean separation of the two beam signals.

SUMMARY OF THE INVENTION

The present invention provides a detector acquisition filter, for use with dual beam CT techniques, that provides the stability of a continuous wave filter and the synchronous sampling capability of an integrate and dump filter. Specifically, the data acquisition filter includes a first and second interruptible filter which operate in either a filtering state or a holding state. When the filters are in the filtering state, their output depends on the frequency components of the detector signal only during the current and previous filtering states. In the holding state, the output of the filter is the last output value of the filter during the previous filtering state. When the x-ray beam of the CT machine is in a first state the first interruptible filter is in the filtering state and the second interruptible filter is in the holding state and the opposite holds true when the x-ray beam is in the second state. In one embodiment a switch provides a single sampling output connected alternately to the filter that is in the hold state.

It is one object of the invention, therefore, to provide a means of filtering a discontinuous detector signal produced by two rapidly alternated x-ray beam states.

Preferably, each of the two interruptible filters shares a preamplifier for receiving the detector signal and includes a switchable feedback element for receiving feedback from the interruptible filter that is in the filtering state.

It is another object of the invention, therefore, to provide a gain stable anti-aliasing filter. A single shared feedback element provides close matching of the gain of the first and second interruptible filters. The interruptible filters may be controlled by a single resistive feedback element to provide higher stability than that provided by a capacitive and resistive feedback element such as is used in an integrate and dump filter design.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 3 is a plot of ray angle T and radius r of the projection data acquired with the CT system of FIG. 1 using the technique of focal spot "wobbling" and showing the periods associated with the two beam states;

FIG. 4(a) is a representational plot of a detector signal produced by a detector element during the wobbling technique of FIG. 3 showing the interleaving of the data for the two beam states;

FIG. 4(b) is a plot similar to that of FIG. 4(a) showing the effective input seen by one interruptible filter of the present invention receiving the signal of FIG. 4(a);

FIG. 4(c) is a representational plot of the output of the interruptible filter of the present invention receiving the input of FIG. 4(a);

DETAILED DESCRIPTION OF THE PREFERRED EMBODIMENT

Figure 1:
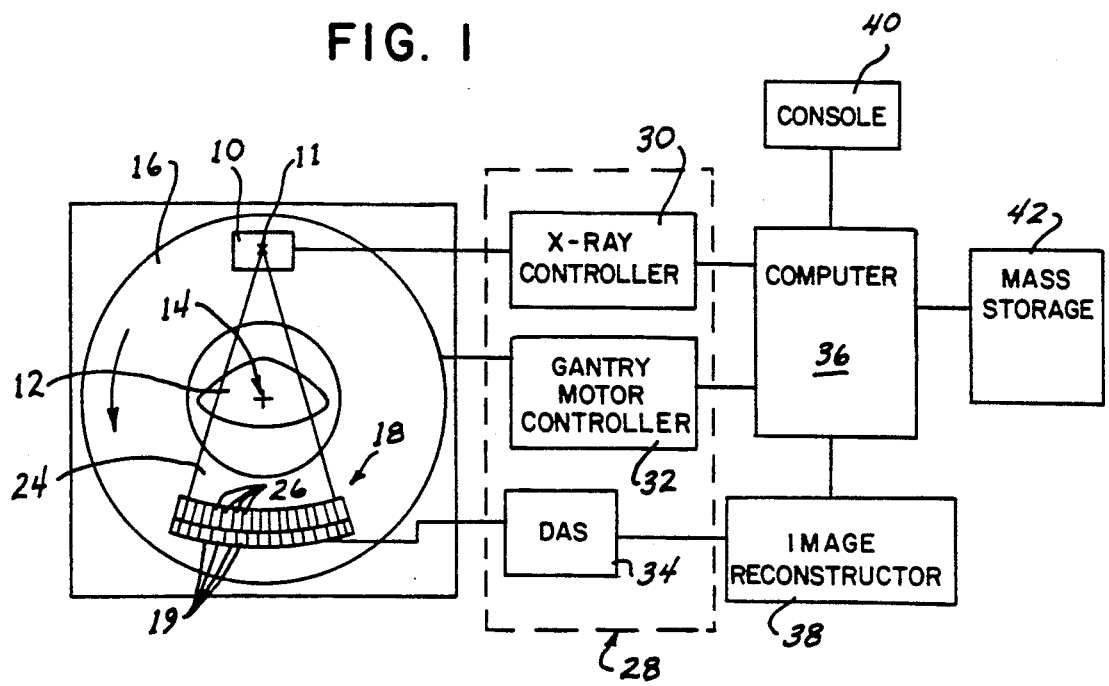
FIG. 1 is a schematic representation of a CT system suitable for use with the present invention.

Referring to FIG. 1, a CT gantry 16, representative of a "third generation" CT scanner includes an x-ray source 10 oriented to project a fan beam of x-rays 24 from a focal spot 11 through imaged object 12 to detector array 18. The detector array 18 is comprised of a number of detector elements 26 which together detect a projected image resulting from the transmission of x-rays through the imaged object 12. Associated with each detector is an interruptible filter 19 as will be more fully described below. The gantry 16 rotates about a center of rotation 14 positioned within the imaged object 12.

The control system of a CT scanner, suitable for use with the present invention, has gantry associated control modules 28 which include: x-ray controller 30 which provides power and timing signals to the x-ray source 10 and which controls the focal spot 11 position within the x-ray tube, gantry motor controller 32 which controls the rotational speed and position of the gantry 16, and the data acquisition system ("DAS") 34 which samples projection data from detector elements 26 of the detector array 18 through the interruptible filters 19 and converts the filtered data to digital words for later computer processing.

The x-ray controller 30 and the gantry motor controller 32 are connected to a computer 36. The computer is a general purpose minicomputer such as the Data General Eclipse MV/7800C.

The DAS 34 is connected to image reconstructor 38 which receives sampled and digitized signals from the DAS 34 to perform high speed image reconstruction according to methods known in the art. The image reconstructor 38 may be an array processor such as is manufactured by Star Technologies of Virginia.

The computer 36 receives commands and scanning parameters via operator console 40 which is generally a CRT display and keyboard which allows the operator to enter parameters for the scan and to display the reconstructed image and other information from the computer 36. A mass storage device 42 provides a means for storing operating programs for the CT imaging system, as well as image data for future reference by the operator.

Figure 2:
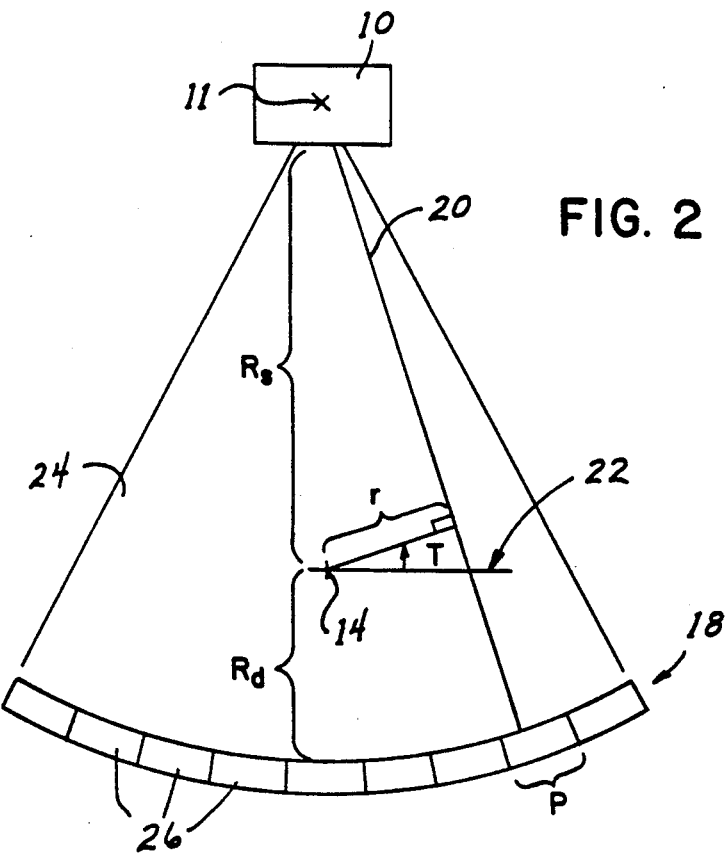
FIG. 2 is a detail of the fan beam of x-rays produced by the system of FIG. 1 showing the relative angles and axes associated therewith.

Referring to FIG. 2, the portion of the fan beam 24 associated with a particular detector element 26 may be identified by a ray 20 along a line through the center of the x-ray focal spot 11 and the center of the particular detector element 26. The ray 20 is described by a radius line of perpendicular distance from the center of rotation 14 of length "r" and an angle of rotation T of that radius from an arbitrary reference axis 22 fixed in space.

The r and T value for each ray 22 may be mapped to an r-T diagram, such as is shown in FIG. 3, having horizontal axis of T and a vertical axis of r. Referring to FIG. 3, at the start of the acquisition of the data for a projection, the ray 20 for a given detector 26 is at position 50 on the r-T diagram. For simplicity, the starting position 50 of only one ray 20 is shown in FIG. 3, however, as is understood in the art, a projection normally includes nearly one thousand rays 20 and corresponding intensity measurement data.

As the gantry 16 rotates, the position of the ray 20 moves horizontally along the r-T diagram from the starting point 50 along horizontal line 52 of gantry rotational angle dT during a first period I. The horizontal line 52 corresponds to increasing T caused by the gantry 16 rotation. The changing intensity of the x-ray radiation along the ray 20 over the horizontal line 52 is received by the detector elements 26. After the gantry 16 has rotated by dT, the position of the focal spot 11 of the x-ray tube 10 with respect to the gantry 16 is shifted, moving the position of ray 20 to a starting location 54 of increased r and decreased T. During a second period II of gantry rotation, the ray 20 moves horizontally from this starting position 54 again by distance dT along horizontal line 56. At the end of this starting position, the focal spot 11 is moved back to the original position with respect to the gantry which because of the intervening rotation of the gantry is at a new position 58 on the r-T diagram at the same r value as the starting position 50 but displaced in T. This process is repeated with the x-ray focal spot 11 moving between a first state during first periods I and a second state during second periods II, the states being defined by the relative position of the x-ray focal spot 11 to the gantry 16.

Referring to FIG. 4(a), the amplitude of the signal 62 from the detector 26 is discontinuous at times t=nΔt where n is an integer and Δt is the time taken for the gantry to move dT. These discontinuities 60 result from the abrupt movement of the x-ray focal spot 11 between states and thus the change of the orientation of the x-ray beam 24 with respect to the imaged object 12 between the first period I and the second period II. As mentioned above, a continuous wave filter receiving this discontinuous signal will tend to combine data from period I and II with the effect of "blurring" the data from the period I with the data from the period II.

Figure 5:
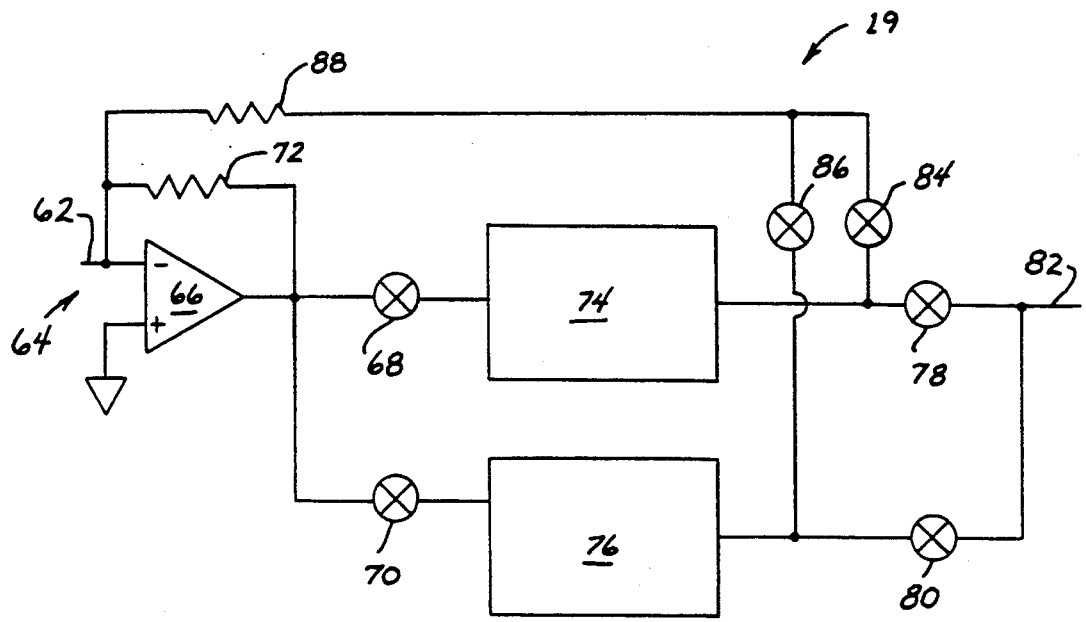
FIG. 5 is a simplified schematic representation of the interruptible filter of the present invention.

Referring now to FIG. 5, the interruptible filter 19 of the present invention receives the detector signal 62 at a detector input 64, the detector signal 64 coming from a detector element 26 in the detector array 18. Additional and separate interruptible filters are associated with each of the remaining detector elements 26 (not shown). The detector signal 62 is amplified by a differential preamplifier 66 which receives the detector signal 62 at its inverting input and which boosts the level of the detector signal 62 to reduce the effect of leakage currents in, and injection currents from, the solid state switches 68 connected to the output of the preamplifier 66. Preamplifier 66 may be any commercially available operational amplifier with low input current, low offset voltage and low offset voltage drift. The non-inverting input of preamplifier 66 is connected to ground.

A resistor 72 provides local feedback around this preamplifier 66 for stability, connecting the output of the preamplifier 66 to its inverting input as will be understood by those of ordinary skill in the art.

The output of the preamplifier 66 is received by the "pole" of single pole single throw ("SPST") solid state switches 68 and 70. The "throws" of these switches 68 and 70 are connected to the inputs of low pass filter subunits 74 and 76 respectively.

The outputs of filter subunits 74 and 76 respectively are in turn connected to one pole of SPST switches 84 and 86 which have their throws connected together and received by the inverting input of the preamplifier 66 through feedback element 88. Accordingly when switch 84 is closed, the feedback signal to the preamplifier 66 is provided by the output of filter subunit 74 and when switch 86 is closed the feedback signal to the preamplifier 66 is provided by the output of filter subunit 76.

It will be understood, therefore, that when switches 68 and 84 are closed the filter subunit 74 is connected in a feedback configuration with preamplifier 66 to form a first filter; and when switches 70 and 86 are closed the filter subunit 76 is connected in a feedback configuration with preamplifier 66 to form a second filter.

The first and second filters are 2-pole low-pass Bessel filters with a frequency cutoff of 1105 Hz. The cutoff frequency is selected in relationship to the sampling frequency of the DAS 34 to provide anti-aliasing properties as have been discussed. Although the shape of the 2-pole Bessel filter is preferred, it will be understood from the following description by those of ordinary skill in the art that other low pass filters such as Butterworth or Tchebycheff may be used.

The first and second filter formed with filter subunits 74 and 76 are also "interruptible", acting as lowpass filters when respective switch 68 or 70 is closed, but "freezing" when respective switch 68 or 70 is open, holding the last previous filtered value occurring at its output prior to the opening of the switch 68 or 70 and preserving its internal values against change with time.

The output of the filter subunits 74 and 76 are received by the poles of SPST solid state switches 78 and 80 whose throws are connected together to provide a single sampling output 82 to the DAS 34 from either filter subunit 74 or filter subunit 76 depending on the period. The switches 78 and 80 take on the opposite state, respectively, as corresponding switches 68 and 70. Switch 78 is open when switch 68 is closed and filter subunit 74 is filtering during period I, and switch 78 is closed when switch 68 is open and filter subunit 74 is in the holding state during period II. Thus, the sampling of the filter subunit 74 output may occur any time during period II yet still provide the filtered value corresponding exactly with the time of the last transition between period I and II. This makes synchronization of the DAS 34 sampling with a particular time or position of the gantry 16 easier than with a continuous wave filter as described above. Such coordination of sampling with the position of the gantry 16 may be useful in eliminating image artifacts from images formed with the spot wobbling techniques referred to above.

In a similar manner, the switch 70 takes the opposite state as switch 80 to allow the sampling of the filter subunit 76 output at any time during period I.

Figure 6:
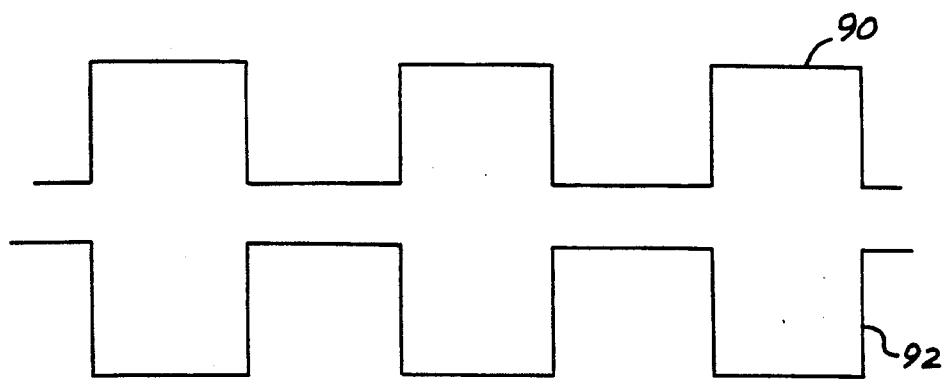
FIG. 6 is a plot of the clock waveform used for synchronizing the interruptible filter of FIG. 5 with the dual beam states of a CT machine.

Referring to FIGS. 5 and 6, switches 68, 84, and 80 are closed synchronously by a clock signal 90 timed to be "on" or high during the first period I and off during the second period II The filter 74 is correspondingly in the filtering state during period I and in the holding state during period II.

Conversely, switches 70, 86, and 78 are closed by a clock signal 92 be which is timed to be on with period II and off with period I, and the filter 76 is in the holding state during period I and in the filtering state during period II. The signals 90 and 92 are square waves phased so that there is no overlap between the on times of the signals 90 and 92 and therefore only one signal 90 or 92 is on at any time.

The operation of the solid state switches is such as to connect either filter subunit 74 or filter subunit 76 with the preamplifier 66 and to provide an appropriate feedback loop through feedback element 88. Filter subunits 74 and 76 have high DC gain and hence the DC gain of the filter 19 will be determined by feedback element 88 regardless of which filter subunit 74 or 76 is connected or of the forward gain through the preamplifier 66 or the filter subunits 74 or 76. The feedback element 88 is predominantly resistive, being largely determined by a single resistor, and hence is a much more stabile gain controlling element than is the capacitor of the integrate and dump circuit previously described.

The circuitry of the filter subunits 74 and 76 are identical. For simplicity, only filter subunit 74 will be described in detail and the operation of filter subunit 76 will be understood from this description.

Figure 7:
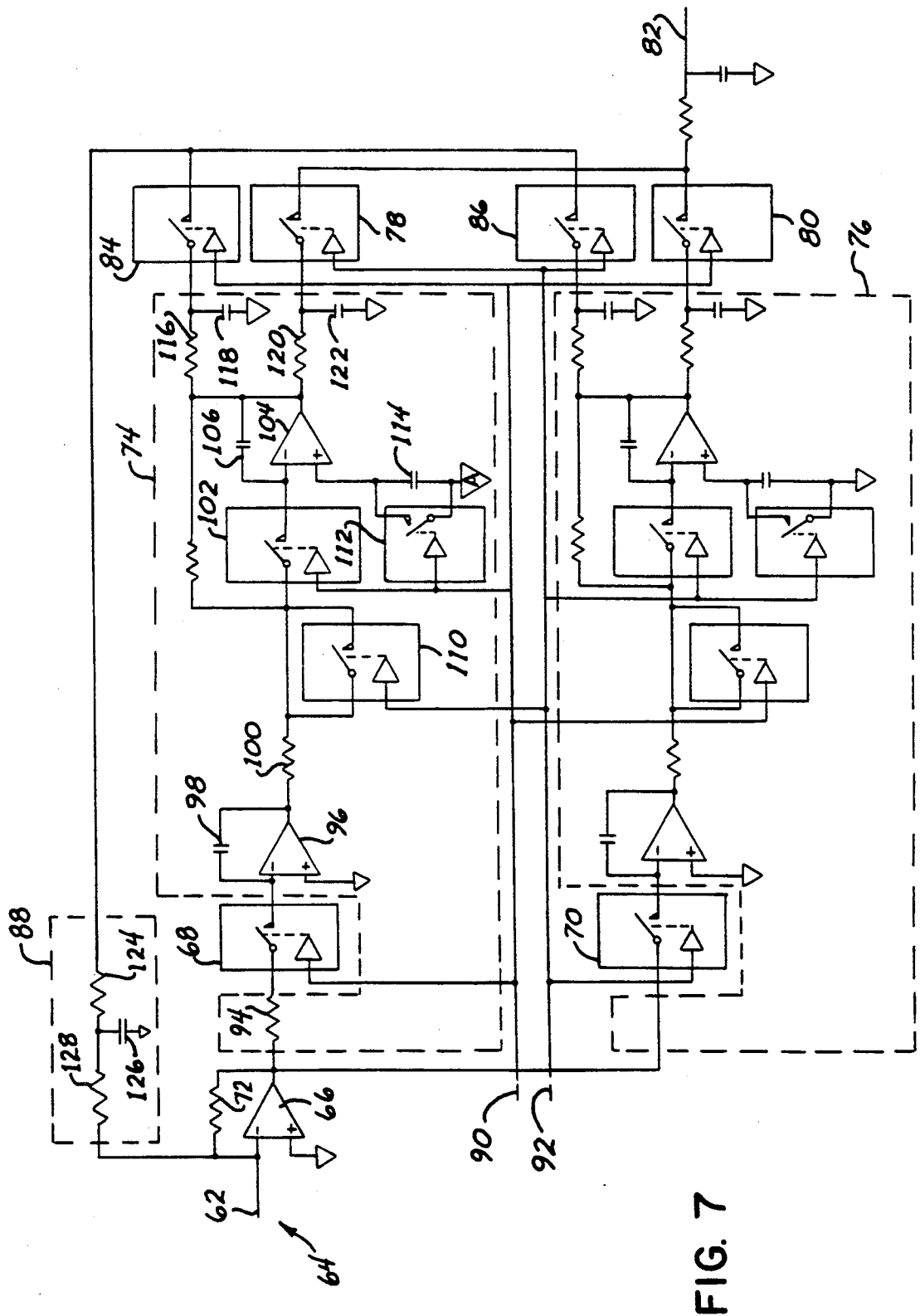
FIG. 7 is a detailed schematic of the interruptible filter of the present invention.

Referring to FIG. 7, the input to the filter subunit 74 connects to an integrator formed of an input resistor 94 connected to the inverting input of a differential amplifier 96, through switch 68. Amplifier 96 has a capacitor 98 connected between its output and its inverting input which serves to integrate the current through resistor 94 as is understood in the art. The non-inverting input of differential amplifier 96 is connected to ground.

Thus when switch 68 is closed, the inverting input of the amplifier 96 receives current from the preamplifier 66 through resistor 94 and integrates that current. When the switch 68 is open, however, the output of the amplifier 96 holds the last value it had prior to the opening of switch 68.

The output of amplifier 96 is connected through resistor 100 and SPST solid state switch 102 to the inverting input of amplifier 104, with the pole of the switch 102 connecting to resistor 100 and the throw of the switch 102 connecting to the inverting input of amplifier 104. A capacitor 106 is connected between the output of amplifier 104 and its inverting input, and a feedback resistor 108 is connected between the output of the amplifier 104 and the pole of switch 102. Thus when switch 102 is open, the resistive feedback path around the amplifier 104 is broken and the amplifier 104 acts like amplifier 96, holding its last output value prior to the opening of the switch 102.

The injection of charge into amplifier 104 by the switching action of the solid state switch 102 is minimized by SPST solid state switches 110 and 112 and components 114-122. Switch 110 has it pole and throw connected to the pole of switch 102 and closes when switch 102 opens to counteract the injection of charge by switch 102. The non- C inverting input of amplifier 104 is also connected to ground through capacitor 114 which is shunted by switch 112 which opens and closes with switch 102.

The output of amplifier 104 is connected to the pole of switch 84 through a network formed of series resistor 116 followed by capacitor 118 to ground. An identical network connects the output of the amplifier 104 to switch 78. These networks also attenuate the effect of the charge injection by the solid state switches 84 and 78.

The feedback element 88 is comprised of a series 10 resistor 124 leading from the throw of switch 84, followed by a capacitor 126 to ground and series resistor at the junction of capacitor 126 and resistor 124 leading to the inverting input of preamplifier 66. It will be seen that the feedback path includes not only resistors 116, 124, and 128, but also capacitor 118 and 126. These capacitors have no effect on the DC gain and negligible effect on the low frequency gain as a result of their small value and the small values of resistors 116 and 124 which are selected to have an RC time constant of approximately 0.05 microseconds.

The cutoff frequency of the Bessel filters, formed by the preamplifier 66 and the filter subunit 74 or 76 in the feedback loop with feedback element 88, is selected to prevent aliasing in the signal that will be sampled by the DAS 34. Accordingly, the cutoff frequency of the Bessel filters may be adjusted with changes in the sampling rate which will depend generally on the speed of the gantry 16 and the number and geometry of the detector elements 26. It will be noted that the operation of switches 68 and 102 essentially "freeze" the operation of the filter formed of the preamplifier 66 and the filter subunit 74 during the period when signal 90 is low. The intermediary values of the filter, specifically the output of amplifiers 96 and 104, do not change with time or changes in the detector input when the signal 90 is low, nor does the intrinsic "memory" of the filter, manifest in the voltage of capacitors 98 and 106, change. This "hold" state of the filter employing either filter subunit 74 or filter subunit 76 permits the use of a simple low pass filter with the discontinuous detector signal 62 as shown in FIG. 4(a).

Referring to FIG. 4(b) the effective input to the filter formed of the preamplifier 66 and the filter subunit 74 is a concatenation of only those segments of detector 10 signal 62 occurring during period I. This is because the filter is frozen in the holding state during period II. Conversely, the effective input to the filter formed of the preamplifier 66 and the filter subunit 76 (not shown) is a concatenation of those segments of detector signal 62 occurring during period II.

Referring to FIG. 4(c) the output of the filter 19 appears as a series of constant voltages reflecting the final outputs of the filter subunits 74 and 76 during the previous filtering state per the current holding state. The relatively long holding state of the filter subunits 74 and 76 allows the sampling of all detector elements 26 within the detector array 18 to be synchronized at the same gantry position, as with an integrate and dump filter, and yet the configuration of the first and second filters allow resistive feedback for stability.

Many modifications and variations of the preferred embodiment which will still be within the spirit and scope of the invention will be apparent to those with ordinary skill in the art. For example, this filter may also be used with dual energy scanning where, for example, the first period I is high x-ray energy and the second period II is low x-ray energy. Also it will be apparent that the filter may be used with other gantry and detector configurations including the so called "translate and rotate" configuration. In order to apprise the public of the various embodiments that may fall within the scope of the invention, the following claims are made.

I claim:

1. A data acquisition filter for a CT imaging system having a first and second x-ray beam activated during a first and second period, the first and second x-ray beams received by a detector producing a detector signal, the data acquisition filter receiving the detector signal and producing a sampling output and comprising:

a clock synchronized with the first and second period for producing a clock signal;

a first and second interruptible filter for receiving the clock signal and a filter output for producing a sampling output, each filter having a filtering state and a holding state, the filter output for each filter dependent on the frequency components of the detector signal only during the current and previous filtering states during the filtering state, and dependant on the last output state; and wherein the first interruptible filter is in the filtering state during the first period and in the holding state during the second period and the second interruptible filter is in the holding state during the first period and the filtering state during the second period.

2. The data acquisition filter of claim 1 including a switch for connecting the first filter output to the sampling output during the first period and connecting the second filter output to the sampling output during the second period.

3. The data acquisition filter of claim 1 wherein the first and second interruptible filters include and share a preamplifier means for amplifying the detector signal and include a switchable feedback element for receiving feedback from the output of the first interruptible filter during the first period and from the second interruptible filter during the second period and providing that feed back to the preamplifier.

4. The data acquisition filter of claim 3 where the feedback element is substantially resistive.

5. The data acquisition filter of claim 1 wherein the interruptible filters act as second order low pass Bessel filters, with cut off frequencies substantially equal to half a rate of sampling, during the filtering state.

6. The data acquisition filter of claim 1 where the first and second x-ray beams are offset in space with respect to each other.

7. The data acquisition filter of claim 1 where the first and second x-ray beams are of different energies.

8. A data acquisition filter for a CT imaging system having dual beam states and a detector signal and a sampling output comprising:

an input differential amplifier for receiving the detector signal and having an output;

a first and second filter subunit;

a switch means for alternately connecting the first and second filter subunit between the output of the input differential amplifier and the sampling output according to the beam state; and a feedback means for providing direct current feedback to the differential amplifier from the output of the connected filter subunit.

9. The data acquisition filter of claim 8 where the feedback means is substantially resistive.

* * * * *